(12) United States Patent
Koike et al.

(10) Patent No.: US 7,138,433 B2
(45) Date of Patent: Nov. 21, 2006

(54) QUINONE-BASED THERAPEUTIC AGENT FOR HEPATOPATHY

(75) Inventors: Yukihiro Koike, Tokyo (JP); Yasushi Shiratori, Okayama (JP); Masao Omata, Tokyo (JP); Toshihiko Mizuta, Saga (JP); Kyosuke Yamamoto, Saga (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 10/662,820

(22) Filed: Sep. 16, 2003

(65) Prior Publication Data

US 2005/0075404 A1 Apr. 7, 2005

Related U.S. Application Data

(60) Provisional application No. 60/410,793, filed on Sep. 16, 2002.

(51) Int. Cl.
*A61K 31/12* (2006.01)
(52) U.S. Cl. ...................................... 514/681
(58) Field of Classification Search ................ 514/681
See application file for complete search history.

(56) References Cited

U.S. PATENT DOCUMENTS 5,021,570 A * 6/1991 Ida et al. .................... 514/681

FOREIGN PATENT DOCUMENTS

| JP | 63-185921 A | 8/1988 |
|---|---|---|
| JP | 06-305955 | 11/1994 |

OTHER PUBLICATIONS

STN Registry File Monograph, RN 863-61-6 (2004).*
Johnson et al., "Relationship Between Drug Activity in NCI Preclinical In Vitro and In Vivo Models and Early Clinical Trials", British Journal of Cancer, (2001) 84(10); 1424-1431.*
"Comparison of Antitumor Activity of Vitamins $K_1$, $K_2$ and $K_3$ on Human Tumor Cells By Two (MTT and SRB) Cell Viability Assays," Felicia Y. - H. Wu et al., Life Sciences, vol. 52 pp. 1797-1804, Pergamon Press 1993.
"Changes of Plasma Des-γ-Carboxy Prothrombin Levels In Patients With Hepatocellular Carcinoma In Repsonse to Vitamin K," Midori Furukawa et al., Cancer, vol. 69, No. 1, pp. 31-38, J.B. Lippincott Company, Philadelphia, Jan. 1, 1992.
"DES-γ-Carboxy Prothrombin As A Useful Predisposing Factor for the Development of Portal Venous Invasion in Patients with Hepatocellular Carcinoma," Yukihiro Koike et al., Cancer, vol. 91, No. 3, pp. 561-569, John Wiley & Sons, Inc., Feb. 1, 2001.
"The Growth Inhibitory Effects of Vitamins K and Their Actions On Gene Expression," Ziqiu Wang et al., Hepatology, vol. 22, pp. 876-882, Sep. 1995.
O'Neil, J.M. et al., The Merck Index Thirteenth Edition, Merck & Co., Inc., 2001 p. 1787, Item 10082 on Vitamin K.
38th Annual Meeting of Liver Cancer Study Group of Japan, Item 110, p. 135, Inhibitory Effect of Vitamin K Injection Against the Recurrence of Hepatocellular Carcinoma, published on May 13, 2002.
Japanese Journal of Gastroenterology, vol. 99 Supplement, Mar. 20, 2002, Item 308, A Clinical Study of the Effects of Vitamin K in Inhibiting Recurrence of Hepatocellular Carcinoma.
ACTA Hepatologica Japonica, vol. 43 Supplement (1) 2002, May 20, 2003, Item O-98, A Randomized Prospective Controlled Study by Vitamin K-II Injection for the Purpose of Preventing Portal Venous Invasion (PVI).
Koike, Y. et al.., "Randomized Prospective Study of Prevention from Tumor Invasion into Portal Vein in 120 Patients with Hepatocellular Carcinoma by Vitamin K Administration," available online at: http://ddw02.agora.com/planner/displayabstract.asp-?presentationid=31 (Apr. 11, 2002).
Copy of Official Action for Russian Application No. 2004136304-15 (039482), Russian Patent and Trademark Office, dated Mar. 29, 2006.
Unverified English translation of Official Action for Russian Application No. 2004136304-15 (039482) (Document AK2) (date not availabe).

* cited by examiner

Primary Examiner—Raymond J. Henley, III
(74) Attorney, Agent, or Firm—Sterne, Kessler, Goldstein & Fox P.L.L.C.

(57) ABSTRACT

With an object of providing an agent for treating hepatic disease by inhibiting occurrence of hepatic disease, in particular portal venous invasion, there is disclosed an agent for treating or preventing hepatic disease containing menatetrenone as an active ingredient thereof. This agent for treating or preventing hepatic disease is effective against hepatic cancer, in particular DCP (des-γ-carboxy prothrombin) positive hepatic cancer. Moreover, the agent for treating or preventing hepatic disease containing menatetrenone as an active ingredient thereof according to the present invention exhibits remarkable effects in improving the prognosis after hepatic cancer treatment, and exhibits excellent effects as an agent for inhibiting the recurrence of hepatic cancer.

4 Claims, 10 Drawing Sheets

FIG.9

RISK RATIO (RR) FOR RECURRENCE OF HEPATIC CANCER
ACCORDING TO COX PROPORTIONAL HAZARD MODEL

|  |  | RR | p | 95% C.I |
|---|---|---|---|---|
| ALL CASES | VK-II NOT ADMINISTERED | 1 | | |
|  | VK-II ADMINISTERED | 0.329 | 0.0013 | 0.167-0.648 |
| HCV CASES | VK-II NOT ADMINISTERED | 1 | | |
|  | VK-II ADMINISTERED | 0.210 | 0.0001 | 0.094-0.468 |

QUINONE-BASED THERAPEUTIC AGENT FOR HEPATOPATHY

BACKGROUND OF THE INVENTION

1. Field of the Invention

The present invention relates to an agent for treating or preventing hepatic disease, and more specifically to an agent for improving hepatic cancer prognosis, having menatetrenone as an active ingredient thereof.

2. Description of the Related Art

It is known that there is a high rate of portal venous invasion (hereinafter referred to as 'PVI') among hepatocellular carcinoma (hereinafter referred to as 'HCC') patients, and once PVI has occurred the prognosis is very poor. It is known that a high des-γ-carboxy prothrombin (hereinafter referred to as 'DCP') level in HCC patients is closely linked to subsequent development of PVI (see Koike Y., Cancer 2001, 91:561-9). DCP is also called PIVKA-II (protein induced by vitamin K absence or antagonist II). DCP is a prothrombin that does not have normal coagulation activity, and is known to increase in level in the case of vitamin K (hereinafter referred to as 'VK') deficiency; DCP is thus a protein that is used as a marker for VK deficiency or impaired VK absorption.

Moreover, it has been reported that if VK is administered to HCC patients with a high DCP level, then the serum DCP level drops (see Cancer 1992, 69:31-8), and that upon administering vitamin K-II (hereinafter referred to as 'VK-II') to a DCP-producing HCC cell line in vitro, cell proliferation is inhibited (see Hepatology 1995, 22:876-82).

However, until now no clinical data had been collected with regard to it being possible, by administering VK-II to patients after HCC treatment, to inhibit the occurrence of PVI, and to inhibit the recurrence of hepatocellular carcinoma, thus improving the prognosis.

In view of the above, it is an object of the present invention to provide an excellent agent for treating or preventing hepatic disease.

SUMMARY OF THE INVENTION

The present inventors accomplished the present invention by being the first to discover that administering an oral VK-II preparation to DCP-producing HCC patients contributes to inhibiting the occurrence of PVI after HCC treatment and improving the prognosis, and moreover inhibits the recurrence of hepatic cancer after treatment.

The above object is attained through an agent for treating or preventing hepatic disease containing menatetrenone as an active ingredient thereof.

According to a preferable aspect of the present invention, in the case of the above agent, the hepatic disease is hepatic cancer.

According to a preferable aspect of the present invention, in the case of the above agent, the hepatic cancer is des-γ-carboxy prothrombin (DCP) positive hepatic cancer.

According to a preferable aspect of the present invention, the above agent improves prognosis after hepatic cancer treatment.

According to a preferable aspect of the present invention, the above agent is an agent that inhibits occurrence of portal venous invasion (PVI).

Moreover, the above object is attained through an agent for inhibiting occurrence of portal venous invasion (PVI) containing menatetrenone as an active ingredient thereof.

Moreover, the above object is attained through an agent for improving survival rate after hepatic cancer treatment containing menatetrenone as an active ingredient thereof.

Moreover, the above object is attained through an agent for inhibiting recurrence of hepatocellular carcinoma containing menatetrenone as an active ingredient thereof.

Moreover, the above object is attained through an agent for reducing DCP level containing menatetrenone as an active ingredient thereof.

Moreover, the above object is attained through a method of preventing portal venous invasion (PVI), comprising administering to a patient an effective dose of a medicine containing menatetrenone as an active ingredient thereof.

Moreover, the above object is attained through a method of inhibiting recurrence of hepatocellular carcinoma, comprising administering to a patient an effective dose of a medicine containing menatetrenone as an active ingredient thereof.

Moreover, the above object is attained through a method of regulating the level of DCP in the blood of a patient, comprising administering to the patient an effective dose of a medicine containing menatetrenone as an active ingredient thereof.

Moreover, the above object is attained through a use of menatetrenone for producing an agent for inhibiting occurrence of PVI.

Moreover, the above object is attained through a method of modulating the level of DCP in the blood of a patient, comprising administering to the patient an effective dose of a medicine containing menatetrenone as an active ingredient thereof.

Moreover, the above object is attained through a use of menatetrenone for inhibiting recurrence of hepatocellular carcinoma.

Furthermore, the above object is attained through an agent for treating or preventing hepatic disease containing a vitamin K as an active ingredient thereof.

Moreover, the above object is attained through a use of menatetrenone for manufacturing an agent for inhibiting occurrence of PVI.

The menatetrenone-containing agent for treating hepatic disease according to the present invention has an excellent effect of inhibiting occurrence of PVI with hepatic disease, in particular DCP positive hepatic cancer, and moreover has an excellent effect of improving the prognosis after hepatic cancer treatment. Furthermore, the menatetrenone-containing agent for treating hepatic disease according to the present invention is very useful in inhibiting recurrence of hepatic cancer after treatment.

BRIEF DESCRIPTION OF THE DRAWINGS

Other objects, features and advantages of the present invention will become more apparent from the following detailed description when read in conjunction with the accompanying drawings, in which:

FIG. 9 shows a diagram indicating results of analyzing the risk ratio (RR) for recurrence using a Cox proportional hazard model.

DESCRIPTION OF THE PREFERRED EMBODIMENTS

Figure 1:
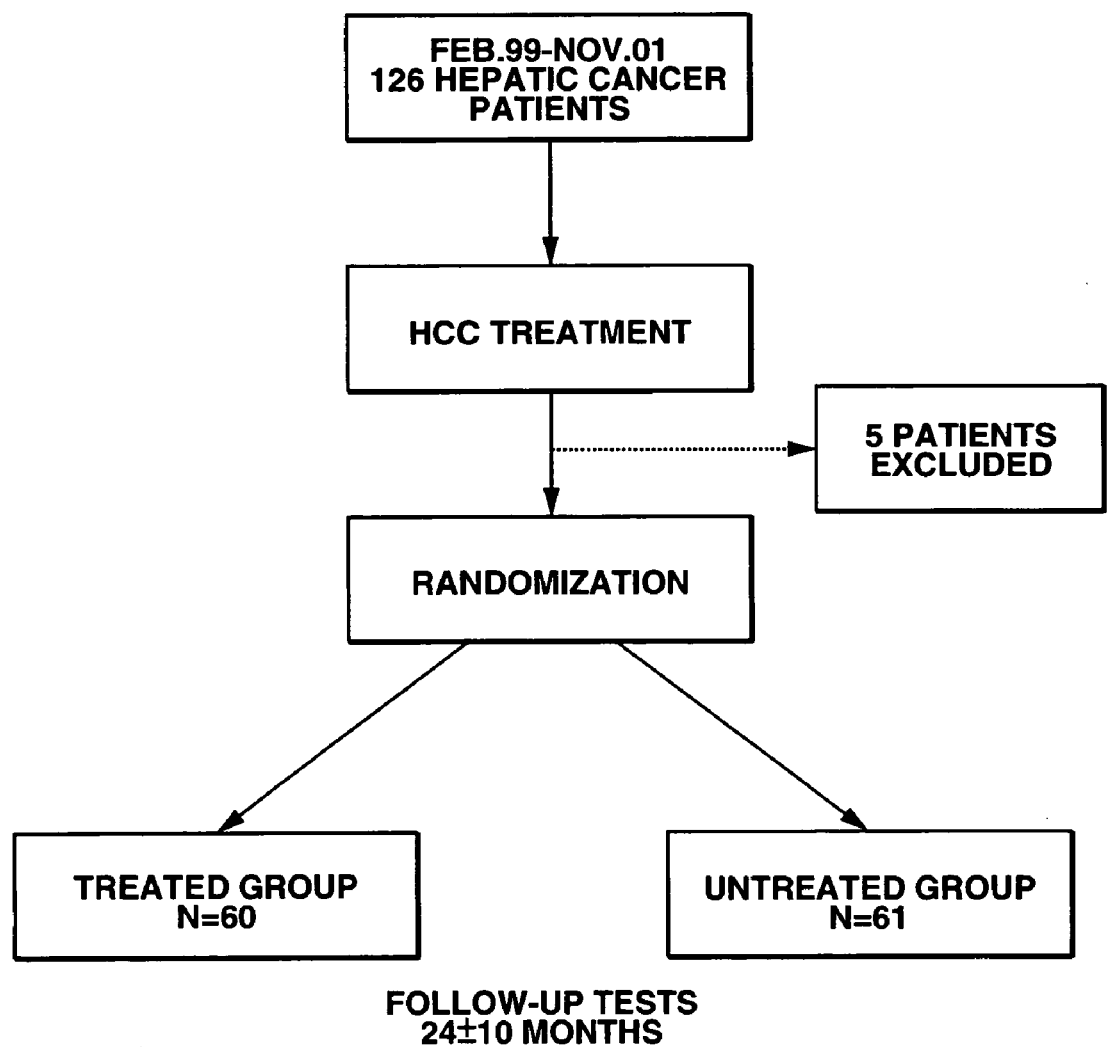
FIG. 1 shows a selection flowchart of the patient.

Following is a more detailed description of the present invention through examples; however, the present invention is not limited to these examples.

Hepatic cancer occurs with a high rate from chronic hepatitis and cirrhosis, which are targeted by the present invention, and having occurred hepatic cancer reoccurs after treatment with a high rate. For example, there are cases of cirrhosis developing from type C hepatitis or type B hepatitis, and there being recurrence after the tumors have been excised. According to the agent for treating hepatic disease of the present invention, the prognosis after such hepatic cancer treatment can be improved very effectively (i.e. recurrence can be prevented or treated). Moreover, the occurrence of PVI, which is one form of recurrence of hepatic cancer with poor prognosis, can be inhibited very effectively.

The menatetrenone used in the present invention has the chemical name 2-methyl-3-tetraprenyl-1,4-naphthoquinone, and has a structural formula as shown below.

Menatetrenone is a yellow crystalline or oily substance, has no taste or odor, and is readily decomposed by light. Moreover, menatetrenone hardly dissolves in water. Menatetrenone is also called vitamin K-II (VK-II), and regarding the pharmacological action thereof, in the process of protein synthesis of blood coagulation factors (prothrombin, VII, IX, X), menatetrenone participates in the carboxylation reaction when glutamic acid residues are converted into physiologically active γ-carboxyglutamic acid, and menatetrenone promotes synthesis in the liver of normal prothrombin and so on, and activates the hemostasis mechanism in a living body, thus physiologically realizing hemostasis.

The menatetrenone that is the active ingredient in the medicine according to the present invention may be in the form of an anhydride or a hydrate. Moreover, menatetrenone has crystal polymorphs, but there is no limitation, with it being possible for the menatetrenone to be in any one of the crystal forms, or a mixture thereof. Furthermore, a metabolite produced through the menatetrenone according to the present invention being decomposed in a living body is also included in the scope of the claims of the present invention.

The menatetrenone used in the present invention can be produced using a publicly known method, and as a representative example, can easily be produced using the method disclosed in Japanese Patent Application Laid-open No. 49-55650; alternatively, the menatetrenone can easily be procured from a chemical manufacturer. Moreover, the menatetrenone can be procured as a pharmaceutical preparation such as a capsule or an injection. Regarding the medicine of the present invention, the menatetrenone may be used as is, or may be made into a pharmaceutical preparation using a commonly used method by blending with ingredients that are commonly used as raw materials of medicinal preparations such as publicly known pharmaceutically permissible carriers and so on (e.g. excipients, binders, disintegrators, lubricants, colorants, flavorings, stabilizers, emulsifiers, absorption promoters, surfactants, pH regulators, preservatives, antioxidants, etc.). Moreover, other ingredients such as vitamins and amino acids may be blended in as required. Examples of the form of the pharmaceutical preparation are tablets, a powder, granules, capsules, a syrup, suppositories, an injection, an ointment, a poultice, and so on.

Moreover, in the present invention, there are no particular limitations on the form of administration of the menatetrenone, although oral administration is preferable. Menatetrenone capsules can be procured as Kaytwo capsules (proprietary name, made by Eisai Co., Ltd.) and Glakay capsules (proprietary name, made by Eisai Co., Ltd.), a menatetrenone syrup can be procured as Kaytwo syrup (proprietary name, made by Eisai Co., Ltd.), and an injection can be procured as Kaytwo N (proprietary name, made by Eisai Co., Ltd.).

6

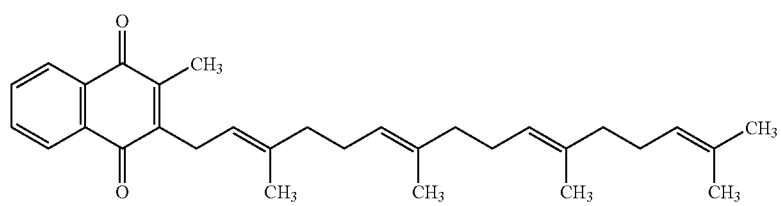

The menatetrenone-containing medicine according to the present invention is useful for treating or preventing hepatic disease. A preferable dose of the menatetrenone is generally 10 to 200 mg/day, more preferably 30 to 135 mg/day.

EXAMPLES

Trial examples of the present invention are given below; however, these trial examples are merely illustrative, and the present invention is not limited thereto. A person skilled in the art could implement the present invention not only through the trial examples shown below, but also with any of various modifications within the scope of the claims appended to the specification of the present application, and such modifications are deemed to be included in the scope of the claims of the present application.

Trial Example 1

A clinical trial (randomized prospective controlled study) was carried out as follows.

Out of patients with hepatocellular carcinoma, ones having a serum DCP level above 60 IU/L (DCP positive hepatic cancer) were included in the trial. On the other hand, patients having portal venous invasion, and patients in which there was already VK metabolism through administration of VK or an anti-VK agent, were excluded from the trial. The details of the trial were as shown in Table 1.

TABLE 1

Trial subjects

Subjects included

1. Hepatic cancer patients
2. Serum DCP level ≧ 60 IU/L

Subjects excluded

1. Portal venous invasion
2. Cancer metastasize out of liver
3. uncontrolled ascites
4. Bilirubin > 3.0 mg/dl
5. Taking vitamin K preparation, warfarin Group administered VK-II Took 45 mg of vitamin K-II (Glakay) three times after hepatic cancer treatment Group not administered VK-II Hepatic cancer treatment only
Judgement criteria 1. Occurrence of portal venous invasion
2. Death FIG. 1 shows a selection flowchart of the patient. 126 hepatic cancer patients were given treatment from February 1999 to November 2001. As the hepatic cancer treatment, percutaneous cauterization therapy (RFA and/or PEIT) for HCC, treatment via the blood vessels (TAE or TAI), or surgical excision was carried out. Of the patients, 5 were excluded from the present trial.

Next, the remaining 121 patients were randomly divided into a treated group (n=60) and an untreated group (n=61). The treated group were orally administered 45 mg/day of VK-II (proprietary name Glakay, made by Eisai Co., Ltd.) after the hepatic cancer treatment, while the untreated group were not administered VK-II.

Follow-up tests were carried out after the hepatic cancer treatment. As the follow-up tests, ultrasonography (abdominal echography) was carried out every 3 months, a CT scan was carried out every 6 months, and the levels of the tumor markers alpha-fetoprotein and DCP were measured every one month.

Table 2 shows the profile of the patients. No important differences were found in any of the clinical parameters between the treated group and the untreated group.

TABLE 2

Patients Profile

| | Treated group (n = 60) | Untreated group (n = 61) | P |
|---|---|---|---|
| Age | 66.9 ± 7.0 | 67.3 ± 7.5 | .8 |
| Sex (male/female) | 36/24 | 45/16 | .12 |
| Virus (HCV/non HCV) | 50/10 | 52/9 | .81 |
| Tumor size (mm) | 32 ± 11 | 35 ± 18 | .27 |
| Number of tumors | 4.0 ± 3.2 | 4.3 ± 3.5 | .66 |
| Child class (A/B or C) | 18/42 | 27/34 | .13 |
| Albumin (g/dl) | 3.4 ± 0.5 | 3.5 ± 0.5 | .3 |
| Bilirubin (mg/dl) | 1.2 ± 0.7 | 1.1 ± 0.9 | .4 |
| ALT (IU/L) | 55 ± 38 | 61 ± 47 | .47 |
| Prothrombin (%) | 78 ± 16 | 78 ± 14 | .99 |
| Blood platelets ($10^4/mm^3$) | 10.8 ± 6.0 | 11.5 ± 6.6 | .52 |
| AFP (ng/L) | 2668 ± 7666 | 1539 ± 7036 | .42 |
| DCP (IU/L) | 985 ± 2639 | 1178 ± 5108 | .80 |
| PTA with/without | 48/12 | 41/20 | .15 | average ± SD (Median)

Figure 2:
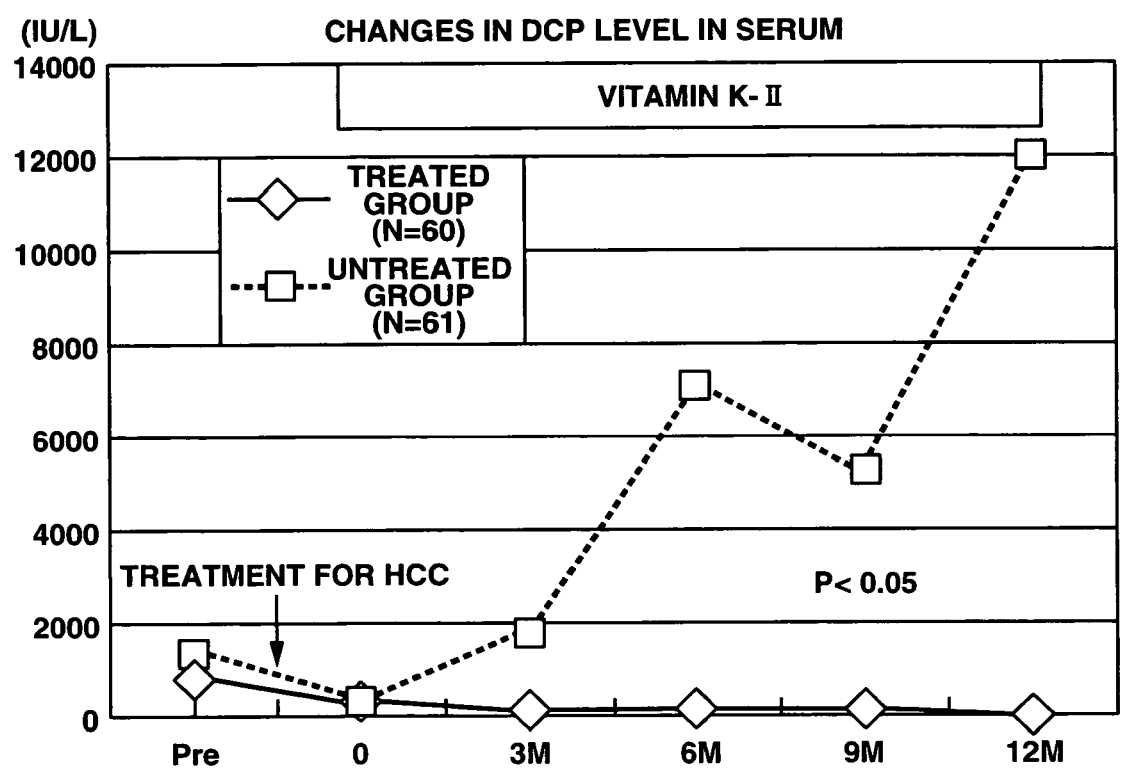
FIG. 2 shows a graph indicating changes in DCP level in serum.

FIG. 2 shows a graph indicating changes in the DCP level in the serum. The solid line is for the treated group, and the dashed line is for the untreated group. For both the treated group and the untreated group, the DCP level dropped after the hepatic cancer treatment. Subsequently, the DCP level remained approximately constant for 12 months for the treated group, whereas the DCP level gradually increased for the untreated group.

Figure 3:
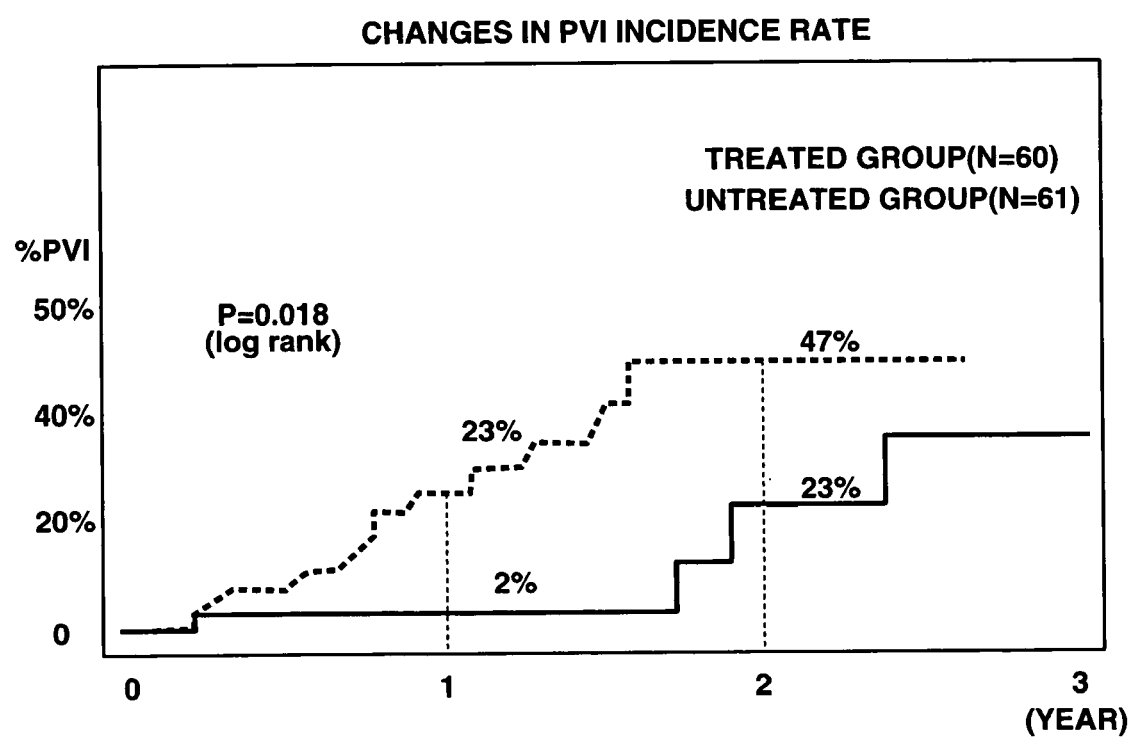
FIG. 3 shows a graph indicating changes in PVI incidence rate.

FIG. 3 shows a graph indicating changes in the PVI incidence rate. As shown in FIG. 3, for the treated group, the PVI incidence rate was 2% after 1 year, and 23% after 2 years. On the other hand, for the untreated group, the PVI incidence rate was 23% after 1 year, and 47% after 2 years (P=0.018).

Figure 4:
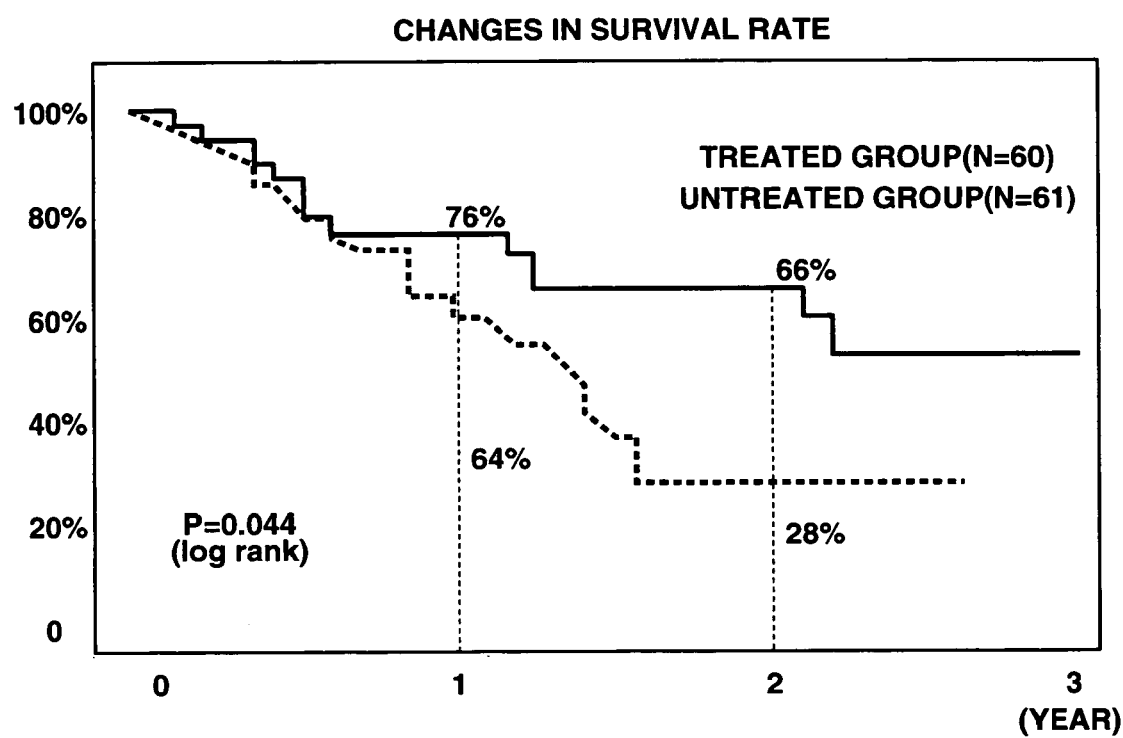
FIG. 4 shows a graph indicating changes in survival rate.

FIG. 4 shows a graph indicating changes in the survival rate. As shown in FIG. 4, the survival rate after 2 years was 66% for the treated group, but 28% for the untreated group (P=0.044).

Statistical analysis was carried out on the PVI incidence rate and the survival rate for the two groups. That is, calculations were carried out using the Cox proportional hazard model, and a test was carried out using the log-rank method. The average observation period was 12±8 months.

From the above results, it is suggested that by orally administering a VK-II preparation, incidence of PVI in DCP positive HCC patients is suppressed very effectively, and moreover survival rate is greatly increased, and hence the prognosis after hepatic cancer treatment is markedly improved.

Trial Example 2

A trial was carried out as follows with an objective of investigating the effect and safety of VK-II in inhibiting recurrence of hepatocellular carcinoma after treatment.

61 cases in which hepatocellular carcinoma was diagnosed and then after treatment therefor necrosis (or curative excision) was judged by contrast CT to have completely occurred were entered from March 1999 to March 2001, the entered cases were divided into two groups, namely a VK-II-administered group for which the end of the patient ID number was an odd number and a non-administered group (control group) for which the end of the patient ID number was an even number, and a VK-II preparation (proprietary name Glakay, made by Eisai Co., Ltd.) was orally administered at a dose of 45 mg/day to the administered group. Contrast CT or MRI was carried out every 3 months, and a statistical analysis of the time period until recurrence was carried out. Specifically, comparison was carried out using the Kaplan-Meier method (log-rank test), and the risk ratio for recurrence was analyzed using the Cox proportional hazard model.

As shown in Table 3, the average observation period for the 61 entered cases (32 cases in the administered group, 29 cases in the non-administered group) was 19.6 months (7–32).

TABLE 3

| Subjects | Administered group (32 cases) | Control group (29 cases) |
|---|---|---|
| Age | 63.3 ± 7.5 (48–75) | 64.5 ± 6.7 (45–74) |
| Sex (male/female) | 23/9 | 18/11 |
| Cause of disease (type C/type B/type B + C) | 28/3/1 | 26/2/1 |
| History of alcohol consumption (addict/non-addict) | 10/22 | 3/26 |
| First occurrence/recurrence | 15/17 | 14/15 |
| Tumor size (mm) | 17.7 ± 5.1 (10–30) | 19.4 ± 6.9 (10–38) |
| Number of tumors | 1.50 ± 0.88 (1–4) | 1.48 ± 0.74 (1–3) |
| Log AFP (ng/ml) | 1.47 ± 0.61 (0.60–3.09) | 1.72 ± 0.91 (0.48–3.88) |
| PIVKA-II (mAU/ml) | 41.8 ± 65.4 (8–346) | 70.3 ± 104.1 (7–417) |
| Liver function (LD A/B/C) | 15/16/1 | 13/15/1 |
| Treatment method (excision/non-excision) | 1/31 | 3/26 |
| Average observation period (months) | 24.3 ± 7.1 (13–37) | 24.2 ± 8.3 (12–37) |

Upon calculating cumulative recurrence rates, the 1-year recurrence rate was found to be 12.5% for the VK-II-administered group and 55.2% for the control group, and the 2-year recurrence rate was found to be 39.6% for the VK-II-administered group and 85.5% for the control group. From these results, it was found that the hepatic cancer cumulative recurrence rate was statistically significantly suppressed for the VK-II-administered group compared with the control group.

Figure 5:
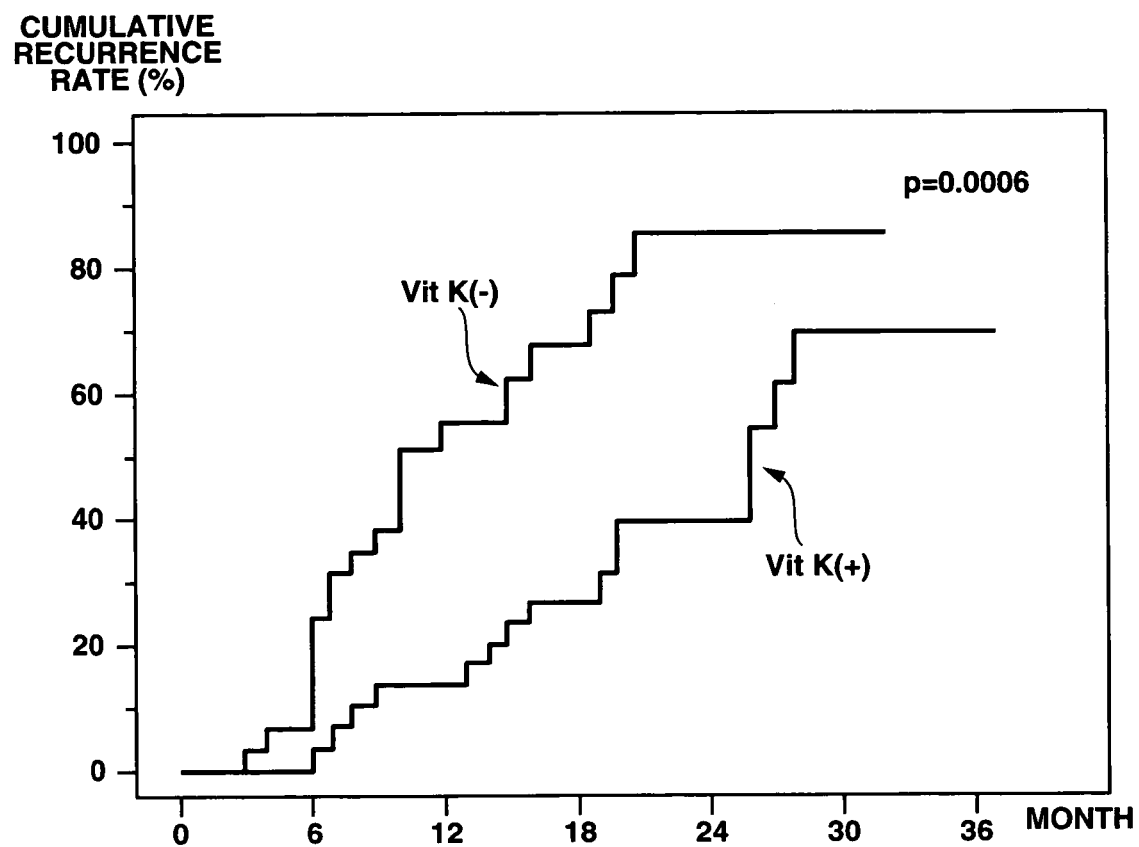
FIG. 5 shows graph indicating the effect of VK-II administration on hepatic cancer recurrence inhibition (50% recurrence)

FIG. 5 shows a graph indicating the effect of VK-II administration on hepatic cancer recurrence inhibition (50% recurrence). As shown in FIG. 5, the time period until 50% recurrence was 26 months for the VK-II-administered group, but was 10 months for the control group.

Moreover, upon calculating the hepatic cancer cumulative recurrence rates considering only HCV cases (type C hepatitis cases), the 1-year recurrence rate was found to be 7.1% for the VK-II-administered group and 61.5% for the control group, and the 2-year recurrence rate was found to be 37.8% for the VK-II-administered group and 87.2% for the control group. From these results, it was found that, even when considering only HCV cases, the hepatic cancer cumulative recurrence rate was statistically significantly suppressed for the VK-II-administered group compared with the control group.

Figure 6:
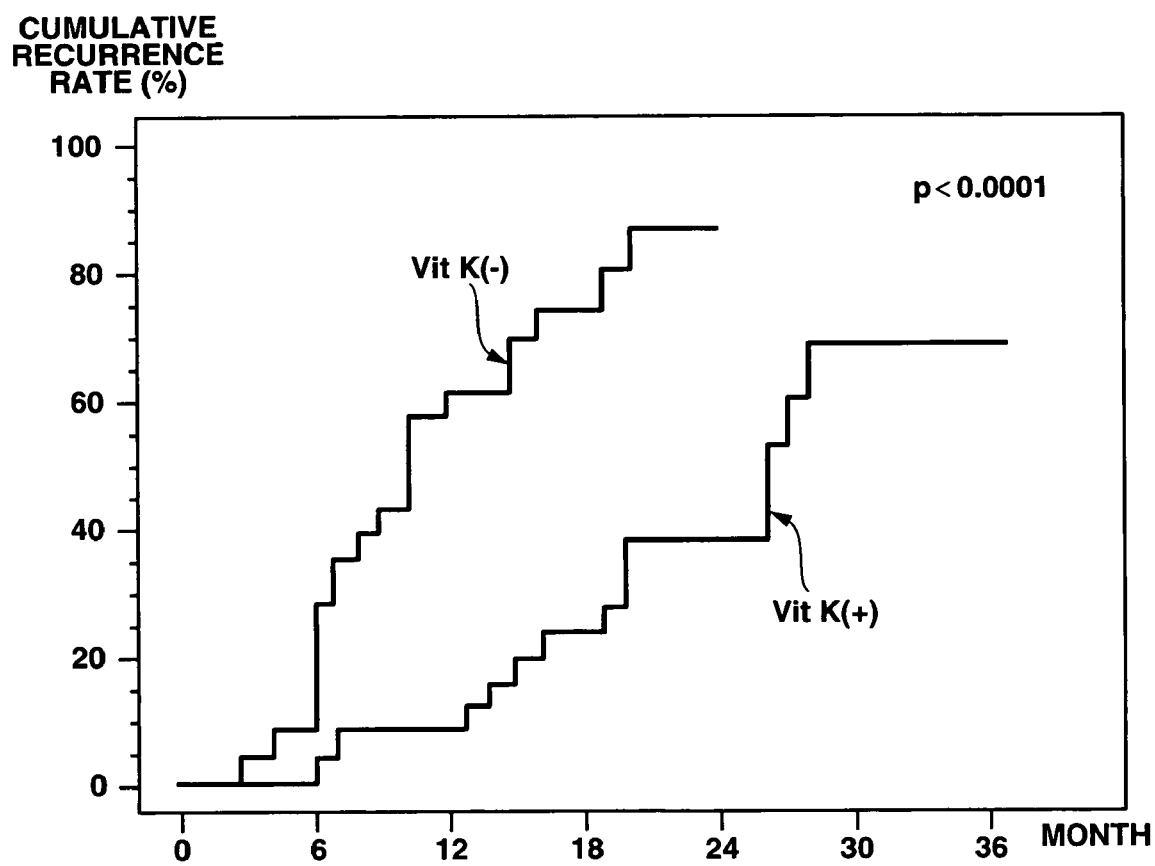
FIG. 6 shows a graph indicating results for HCV cases only in the trial to verify the effect of VK-II administration on hepatic cancer recurrence inhibition (50% recurrence)

FIG. 6 shows a graph indicating the results for the HCV cases only in the trial to verify the effect of VK-II administration on hepatic cancer recurrence inhibition (50% recurrence). As shown in FIG. 6, the time period until 50% recurrence was 26 months for the VK-II-administered group, but was 10 months for the control group.

FIG. 9 shows a diagram indicating the results of analyzing the risk ratio (RR) for recurrence using the Cox proportional hazard model. As shown in FIG. 9, taking the risk ratio for recurrence of hepatic cancer to be 1 for the control group, this risk ratio is approximately one third of that at 0.329 for the VK-II-administered group; in particular, considering only the HCV cases, the risk ratio becomes 0.210, i.e. is reduced to approximately one fifth, by administering VK-II.

Figure 7:
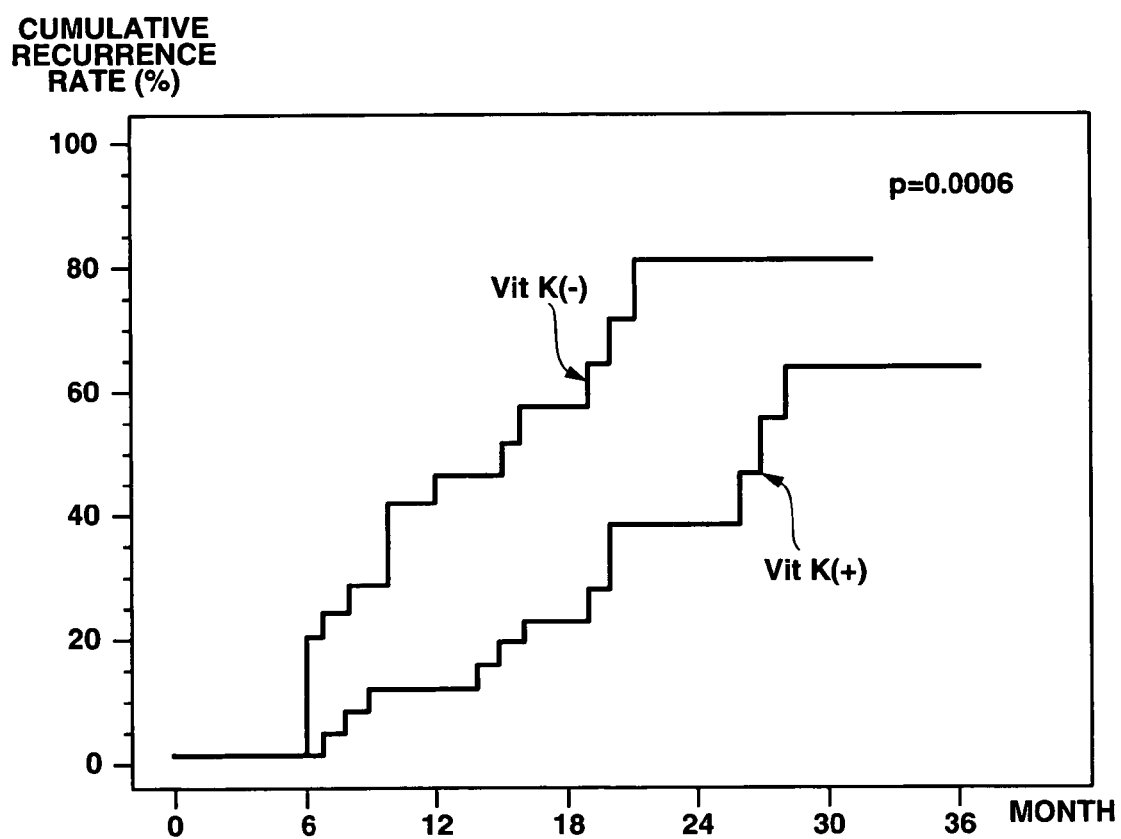
FIG. 7 shows a graph indicating results in the case of excluding cases of local recurrence in the trial to verify the effect of VK-II administration on hepatic cancer recurrence inhibition (50% recurrence)
Figure 8:
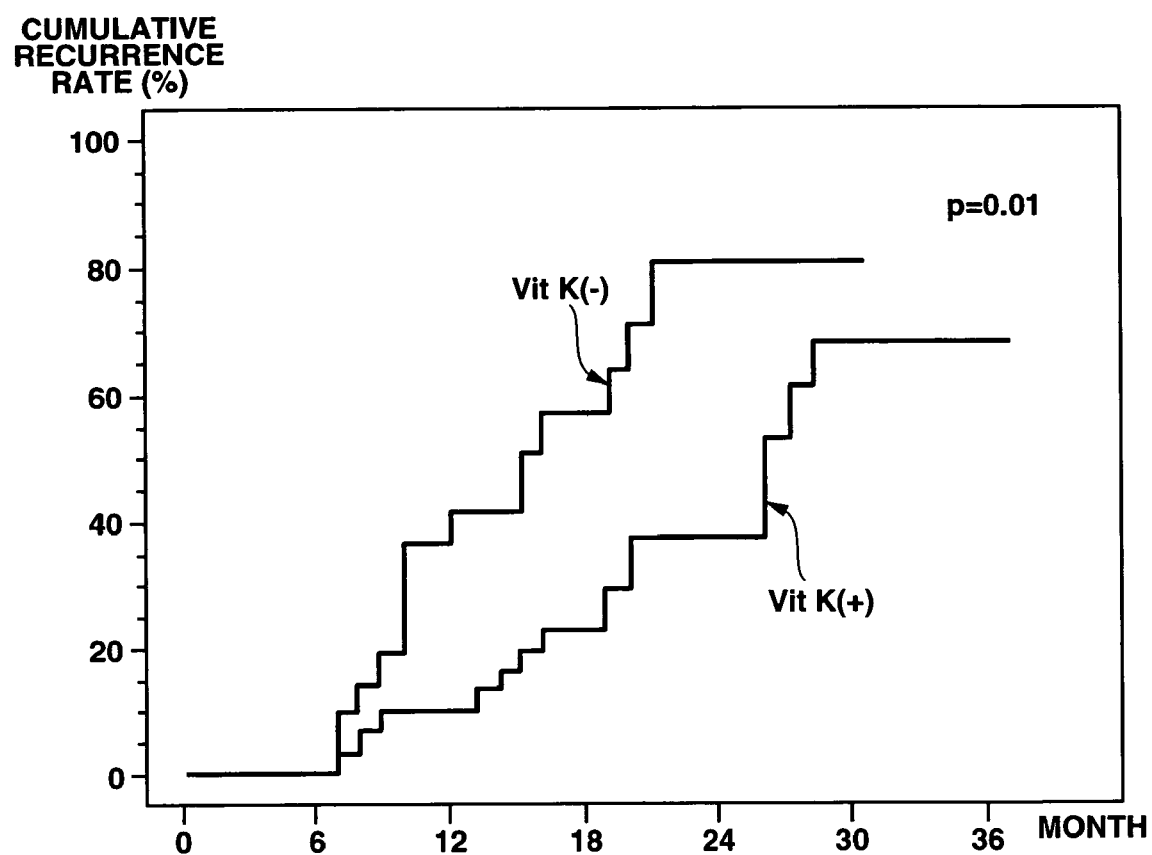
FIG. 8 shows a graph indicating results in the case of excluding cases of recurrence within 6 months in the trial to verify the effect of VK-II administration on hepatic cancer recurrence inhibition (50% recurrence)

FIG. 7 shows a graph indicating the results in the case of excluding cases of local recurrence in the trial to verify the effect of VK-II administration on hepatic cancer recurrence inhibition (50% recurrence) (VK-II-administered group: 29 cases, non-administered group: 22 cases). Moreover, FIG. 8 shows a graph indicating the results in the case of excluding cases of recurrence within 6 months in the trial to verify the effect of VK-II administration on hepatic cancer recurrence inhibition (50% recurrence) (VK-II-administered group: 31 cases, non-administered group: 22 cases). As shown in FIGS. 7 and 8, in these cases, again the hepatic cancer cumulative recurrence rate was statistically significantly suppressed for the VK-II-administered group compared with the control group.

Figure 10:
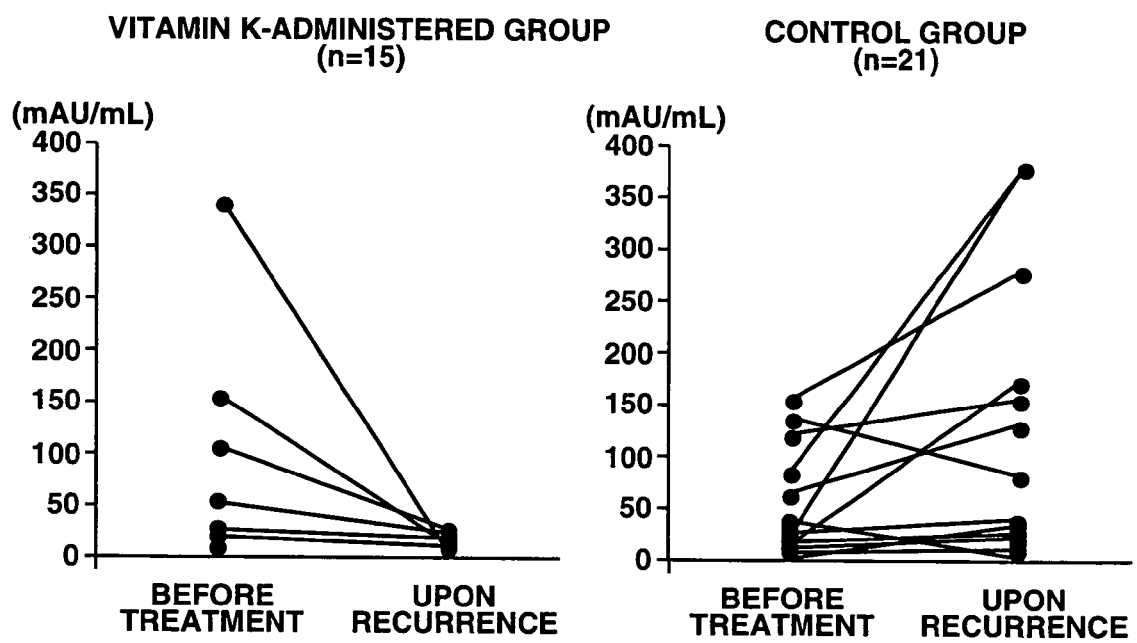
FIG. 10 shows graphs indicating results of analyzing the DCP level before treatment and upon recurrence.

FIG. 10 shows graphs indicating the results of analyzing the DCP level before treatment and upon recurrence. As shown in FIG. 10, with all of the cases of recurrence in the VK-II-administered group, DCP was negative, and moreover there were no side effects, and there were no dropout.

The action of VK-II according to the present application with regard to invasion/metastasis of hepatic cancer cells was studied in vitro. The action on invasion ability was investigated through an invasion assay using HepG2 cells and a Matrigel chamber. The results were that it was found that the number of cells passing through the Matrigel dropped upon adding VK-II, with the drop depending on the concentration of the VK-II. Regarding the action on the metastasis ability, the action of VK-II on the expression of extracellular matrix metalloproteinases (MMPs) was investigated using the Western blot method. Upon investigating the MMP-1 and MMP-3 protein expression in the case of adding VK-II to hepatic cancer cells, it was found that the expression was inhibited. From the above, although the data is in vitro, it can be presumed that VK-II inhibits invasion/metastasis of hepatic cancer cells.

As described above, the menatetrenone-containing agent for treating or preventing hepatic disease according to the present invention has an excellent effect of inhibiting occurrence of PVI with hepatic disease, in particular DCP positive hepatic cancer, and moreover has an excellent effect of improving the prognosis after hepatic cancer treatment.

Furthermore, the menatetrenone-containing agent for treating hepatic disease according to the present invention is very useful in inhibiting recurrence of hepatic cancer after treatment.

What is claimed is:

1. A method of inhibiting recurrence of hepatocellular carcinoma, comprising administering an effective dose of a medicine containing menatetrenone to a patient who had hepatocellular carcinoma and was subjected to treatment of hepatocellular carcinoma in the past.

2. The method of claim 1, wherein said effective dose of said medicine containing menatetrenone comprises the administration of generally 10 to 200 mg of menatetrenone per day to said patient.

3. The method of claim 2 wherein said effective dose of a medicine containing menatetrenone comprises the administration of generally 30 to 135 mg of menatetrenone per day to said patient.

4. The method of claim 3, wherein said effective dose of a medicine containing menatetrenone comprises the administration of 45 mg of menatetrenone per day to said patient.

* * * * *